| United States Patent [19] | [11] | 4,455,305 |
|---|---|---|
| Rokos | [45] | Jun. 19, 1984 |

[54] COMPOSITION FOR THE TREATMENT OF COLITIS ULCEROSA, ENTERITIS REGIONALIS CROHN (MORBUS CROHN), CHRONIC NONSPECIFIC COLITIS AND DIVERTICULITIS AND THE USE OF SALICYLAZOBENZOIC ACID FOR THE PREPARATION OF SUCH COMPOSITIONS

[75] Inventor: Hartmut Rokos, Berlin, Fed. Rep. of Germany

[73] Assignee: Henning Berlin GmbH Chemie- und Pharmawerk, Berlin, Fed. Rep. of Germany

[21] Appl. No.: 281,684

[22] Filed: Jul. 9, 1981

[30] Foreign Application Priority Data

Jul. 17, 1981 [DE] Fed. Rep. of Germany ....... 3027013

[51] Int. Cl.$^3$ ............................................ A61K 31/655
[52] U.S. Cl. .................................................... 424/226
[58] Field of Search ......................... 424/226; 268/207

[56] References Cited

PUBLICATIONS

Raju et al., Azo Dyes Analytical Reagents for Aluminium and Beryllium, Current Sci., 29:52–53, 1960.

*Primary Examiner*—Albert T. Meyers
*Assistant Examiner*—John W. Rollins
*Attorney, Agent, or Firm*—Marshall, O'Toole, Gerstein, Murray & Bicknell

[57] ABSTRACT

Salicylazobenzoic acid is more useful than salazosulfapyridine for the treatment of colitis ulcerosa, enteritis regionalis (Morbus Crohn), chronic nonspecific colitis and diverticulitis. Salicylazobenzoic acid is used in the form of tablets and dragëes or enemae in which it may be used in the form of free acid, compatible salts or mixtures thereof.

8 Claims, No Drawings

COMPOSITION FOR THE TREATMENT OF COLITIS ULCEROSA, ENTERITIS REGIONALIS CROHN (MORBUS CROHN), CHRONIC NONSPECIFIC COLITIS AND DIVERTICULITIS AND THE USE OF SALICYLAZOBENZOIC ACID FOR THE PREPARATION OF SUCH COMPOSITIONS

BACKGROUND OF THE INVENTION

The present invention relates to a novel composition for the treatment of colitis ulcerosa, enteritis regionalis Crohn (Morbus Crohn), chronic nonspecific colitis and diverticulitis containing as the active ingredient salicylazobenzoic acid and/or its physiologically acceptable salts and usual carriers, vehicles or diluents therefor. The invention further relates to the use of salicylazobenzoic acid and/or its physiologically acceptable salts for the preparation of pharmaceutical compositions for the treatment of these diseases.

Salazosulfapyridine has been previously used as the standard preparation for the treatment of these diseases. This compound is administered orally in most cases and probably cleaved by bacteria in the colon to form the two metabolites, 5-aminosalicylic acid and sulfapyridine. Seemingly the metabolite 5-aminosalicylic acid is the active component while the side effects observed in many cases are due to the sulfapyridine metabolite; see KHAN et al, Lancet 2, 892 (1977). Since 5-aminosalicylic acid is instable and substantially incapable of being transferred into the colon by the oral route, KHAN, loc.cit., considered already the possibility of synthesizing a new substance which does not exhibit these disadvantages of the known salazosulfapyridine.

SUMMARY OF THE INVENTION

It has now been found that salicylazobenzoic acid and/or its physiologically acceptable salts are excellently suited to replace the salazosulfapyridine. It has further been found that the cleavage of salicylazobenzoic acid by intestinal bacteria proceeds about twice as rapidly as that of salazosulfapyridine so that the active metabolite, 5-aminosalicylic acid, is very rapidly liberated at the place desired. The second metabolite, 4-aminobenzoic acid, is obviously less toxic than sulfapyridine and, therefore, does not lead to the known side effects of salazosulfapyridine. Comparable with salazosulfapyridine, salicylazobenzoic acid is substantially not absorbed in the small intestine so that it is transferred unchanged into the colon with its bacterial flora.

Salicylazobenzoic acid is a known substance which has been used as dye for the analytical determination of magnesium, aluminum and beryllium; see I. M. Korenman, E. I. Levina, Azo dyes-derivatives of chromotropic and salicylic acids as the reagents for magnesium. Uchenye Zapiski Gor'kovsk. Gosudarst. Univ. im. Ni. I. Lobachevskogo, Ser. Khim. 1958, No. 32, 149–160. N. Appala Raju, K. Neelakantam, Azo Dyes as analytical reagents for aluminum and beryllium. Current Sci. (India) 29, 52–3 (1960).

Despite the fact that the substance per se is known, it was not predictable that it is excellently suitable as a drug for the treatment of colitis ulcerosa, enteritis regionalis Crohn (Morbus Crohn), chronic nonspecific colitis and diverticulitis. It was not before the studies having now been carried out that it was found that salicylazobenzoic acid is cleaved in an analogous manner by intestinal bacteria into the active ingredient, i.e. aminosalicylic acid, and a non-toxic and ineffective metabolite, i.e. 4-aminobenzoic acid. It has further been found only now that this cleavage proceeds at about twice the rate as that of the known active ingredient, salazosulfapyridine. It was by no means predictable that also this substance of a relatively low molecular weight is substantially not absorbed in the small intestine and, therefore, is able to exert its action only locally in the colon and rectum. This is particularly surprising since the solubility of salicylazobenzoic acid in water is higher than that of salazosulfapyridine. However, the higher water-solubility is found to be a further advantage in preparing pharmaceuticals because, e.g. in preparing enemae, substantially higher concentrations per unit volume of enema can be incorporated and, when preparing tablets or dragées, a very high content of active ingredient per unit weight of tablet or dragée can be chosen without affecting thereby detrimentally the dissolution of the tablet in the intestinal tract.

Since the cleavage of the salicylazobenzoic acid should anyhow take place not before the colon and rectum, the tablets and dragées according to the invention are preferably soluble in the small intestine. For this purpose, use is made, for example, of a recipe where the substance are dissolved only in the alkaline environment of the small intestine. However, it is more convenient to accomplish this object by coating the tablets or dragées with a film which is soluble in the small intestine.

Salicylazobenzoic acid may be used in accordance with the invention not only in the free form but also in the form of its physiologically acceptable salts. The alkali metal, alkaline earth metal and ammonium salts are preferably suited. However, any other relatively readily water-soluble salt of physiologically acceptable bases may also be used on principle. Especially when preparing enemae, it may be advantageous to use a mixture of the free salicylazobenzoic acid with a salt to optimize the pH value. However, the oral compositions may also contain wholly or partially the crystalline salts of salicylazobenzoic acid in place of the free acid.

When preparing the compositions according to the invention, all conventional adjuvants for the preparation of tablets and dragées may be used. These conventional adjuvants include talc, starch, cellulose, polyvinyl pyrrolidone, polyvinyl polypyrrolidone, magnesium stearate, etc. For preparing compositions which are soluble in the small intestine, polycarboxylic acids and other polymers which can be cleaved or dissolved only in the alkaline region are particularly suitable. The conventional film coatings which are soluble in the small intestine also consist in most cases of such acidic polymers which are dissolved or cleaved only in the alkaline environment of the small intestine.

The tablets or dragées according to the invention contain generally 0.3 to 1 g. of salicylazobenzoic acid. For the treatment of acute inflammatory processes, 1 to 6 grams of salicylazobenzoic acid are daily administered orally to adults. For the recidivous prophylaxis in permanent therapy, 1 to 4 grams distributed in a plurality of individual doses over the day are sufficient. Since the side effects previously observed in the treatment with salazosulfapyridine were not observed with the compositions according to the invention, higher dosages than heretofore can be administered according to the invention.

The treatment is generally effected orally using preferably tablets or film dragées which are soluble in the small intestine. Under special circumstances, especially if the residence time in the intestine is largely reduced, tablets and dragées which are soluble in the stomach may also be used.

The introduction of enemae may also be used in place of the oral treatment, especially in case of stationary treatment. In this case, up to 100 ml of enema may be introduced once or repeatedly per day. Such an enema should contain 1 to 6 and preferably 3 grams of salicylazobenzoic acid in 100 ml of solution. Thus, prepared enemae should contain 10 to 60 grams and preferably 30 grams of salicylazobenzoic acid per liter of enema.

Toxicity tests with salicylazobenzoic acid which were made also in comparison with the previously used salazosulfapyridine had the following result: In the Ames test, a mutagenous effect of salicylazobenzoic acid could not be observed.

Salicylazobenzoic acid is compatible after repetitive rectal administration to the rabbit intestine. Primary skin irritations and primary mucous membrane irritations were not observed. The determination of the acute toxicity after oral administration to rats at a dosage of up to 10 grams/kilogram did not result in mortalities, indications to incompatibilities and deviations from normal findings. Determination of the subacute toxicity on rats resulted in a "No effect dosis" of 500 mg./kg. Determination of the absorption of salicylazobenzoic acid in the tied-off intestine loop of the jejunum of rats had the result that the substance is not absorbed in the small intestine in contrast to other azo derivatives of salicylic acid.

The azo cleavage of salicylazobenzoic acid in a feces suspension had the result that the substance is no longer detectable as early as after 60 minutes while salazosulfapyridine is no longer detectable after as long as 120 minutes. The half-life periods of the azo cleavage were only 15 minutes for salicylazobenzoic acid while they are 27 minutes for salazosulfapyridine.

It is clearly obvious from these examinations of absorption and cleavage, that salicylazobenzoic acid has a substantially more favorable therapeutic index than the previously used salazosulfapyridine.

Salicylazobenzoic acid is prepared by processes which are known per se by diazotization and coupling with salicylic acid. A typical method of preparation and typical examples of the preparation of compositions according to the invention are described in the examples which follow.

EXAMPLE 1

Preparation of salicylazobenzoic acid

230 Grams of 4-aminobenzoic acid are suspended in 1200 ml of water and 1 kg. of ice and mixed with 410 ml of concentrated hydrochloric acid. While additionally cooling externally, 117 g. of sodium nitrite dissolved in 700 ml of water are slowly added while stirring and maintaining the temperature between −5° and 0° C.

240 Grams of salicylic acid are dissolved in 4500 ml of cold 2 mole/liter of sodium hydrochloride solution. While intensively cooling externally and vigorously stirring, the diazonium salt solution mentioned above is added. The temperature during the addition should be about 0° C. After all of the diazonium solution has been added, stirring is continued for further 2 hours without further cooling.

The salicylazobenzoic acid is precipitated by slowly adding dilute hydrochloric acid until the pH of the solution is about 2.5. The precipitate is filtered by suction and thoroughly washed with water. The yield is 423 grams or 87%. To further purify the product, it is dissolved in dilute ammonia, treated with activated charcoal, filtered by suction and again precipitated with dilute hydrochloric acid.

Analysis: $C_{14}H_{10}N_2O_5$: Calculated: C, 58.74, H, 3,52, O, 27.94; Found: C, 58.62, H, 3.64, O, 27.67.

EXAMPLE 2

Film dragées
(1) Composition per core

| | |
|---|---|
| 500 mg. | of salicylazobenzoic acid (100%, anhydrous) |
| 50 mg. | of cellulose powder, DAB 8 |
| 20 mg. | of polyvinyl polypyrrolidone |
| 20 mg. | of polyvinyl pyrrolidone |
| 10 mg. | of magnesium stearate |
| 600 mg. | |

(2) Preparation
50 kgs. of salicylazobenzoic acid,
5 kgs. of cellulose powder,
1 kg. of polyvinyl polypyrrolidone and
2 kgs. of polyvinyl pyrrolidone
are mixed homogeneously. The mixture is granulated while adding purified water (EAB) and dried at 50° C.
1 kg. of polyvinyl polypyrrolidone and
1 kg. of magnesium stearate
are admixed. The mixture is compressed to dragée cores having a weight of 600 mgs.

The cores are optionally coated by a conventional film coating process with a film which is soluble in the small intestine or in the stomach.

EXAMPLE 3

Enema:
To prepare an enema, the following ingredients are dissolved or suspended in 1000 ml. of water:
30 g. of salicylazobenzoic acid
9 g. of sodium chloride
5 g. of Carbopol 934 ® (neutralized with sodium hydroxide solution (carboxyvinyl polymer)
2 g. of methyl cellulose 25 (water-soluble cellulose ether)
1 g. of Tween 80 ® (polyoxyethylene sorbitan monooleate)
0.5 g. of ascorbic acid
0.4 g. of benzalkonium chloride (50% solution) (benzyl dimethyl alkylammonium chloride)

Amounts of 100 ml. each are filled into bottles and stoppered.

EXAMPLE 4

Enema
To prepare an enema, the following ingredients are dissolved or suspended in about 800 ml. of water:
30 g. of salicylazobenzoic acid
5 g. of Carbopol 934 ® (carboxyvinyl polymer)
2 g. of methyl cellulose 25 (water-soluble cellulose ether)
1 g. of Tween 80 ® (polyoxyethylene sorbitan monooleate)
0.5 g. of ascorbic acid
0.4 g. of benzalkonium chloride (50% solution) (benzyl dimethyl alkyl ammonium chloride)

The mixture is neutralized with sodium hydroxide solution (pH, about 7.3) resulting in a clear solution which is made up with water to 1000 ml.

Amounts of 100 ml. each are filled into bottles and stoppered.

What is claimed is:

1. A pharmaceutical composition in unit dosage form for the treatment of colitis ulcerosa, enteritis regionalis Crohn (Morbus Crohn), chronic nonspecific colitis and diverticulitis, said unit dosage form containing 0.3 to 1 gram of salicylazobenzoic acid, a physiologically acceptable salt thereof or a mixture thereof and a pharmaceutically acceptable adjuvant.

2. A pharmaceutical composition in unit dosage form according to claim 1 in the form of a member of the group consisting of a tablet and a dragée.

3. An aqueous enema containing 10 to 60 grams per liter of dissolved or suspended salicylazobenzoic acid, a physiologically acceptable salt thereof or a mixture thereof.

4. A method of treating colitis ulcerosa, enteritis regionalis Crohn (Morbus Crohn), chronic nonspecific colitis or diverticulitis which comprises orally administering an effective amount of salicylazobenzoic acid, a physiologically acceptable salt thereof or a mixture thereof.

5. A method according to claim 4 in which 0.3 to 1 gram of salicylazobenzoic acid or salt or mixture thereof is orally administered in unit dosage form.

6. A method according to claim 5 in which the unit dosage form is a member of the group consisting of a tablet and a dragée.

7. A method according to claim 4 in which 1 to 6 grams of salicylazobenzoic acid or a salt or mixture thereof is orally administered daily.

8. A method of treating colitis ulcerosa, enteritis regionalis Crohn (Morbus Crohn), chronic nonspecific colitis or diverticulitis which comprises administering an aqueous enema containing an effective amount of dissolved or suspended salicylazobenzoic acid, a physiologically acceptable salt thereof or a mixture thereof.

* * * * *

UNITED STATES PATENT AND TRADEMARK OFFICE
CERTIFICATE OF CORRECTION

PATENT NO. : 4,455,305
DATED : June 19, 1984
INVENTOR(S) : HARTMUT ROKOS

It is certified that error appears in the above-identified patent and that said Letters Patent is hereby corrected as shown below:

On the title page:

The German application priority filing date is changed from "July 17, 1981" to --July 17, 1980--.

Signed and Sealed this

Thirteenth Day of November 1984

[SEAL]

Attest:

GERALD J. MOSSINGHOFF

Attesting Officer

Commissioner of Patents and Trademarks